United States Patent
Thomas et al.

(10) Patent No.: US 10,925,702 B2
(45) Date of Patent: *Feb. 23, 2021

(54) DENTAL VALVE DEVICE HAVING A FLEXIBLE TUBING

(71) Applicant: Stoma Ventures, LLC, Chesterfield, MO (US)

(72) Inventors: Charles Thomas, Vero Beach, FL (US); Edward Arguello, Weston, FL (US)

(73) Assignee: STOMA VENTURES, LLC, Chesterfield, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/161,442

(22) Filed: Oct. 16, 2018

(65) Prior Publication Data

US 2019/0054287 A1 Feb. 21, 2019

Related U.S. Application Data

(63) Continuation-in-part of application No. 16/001,087, filed on Jun. 6, 2018, now Pat. No. 10,799,694, which
(Continued)

(51) Int. Cl.
| | |
|---|---|
| *A61C 17/12* | (2006.01) |
| *A61C 17/06* | (2006.01) |
| *F16K 15/18* | (2006.01) |
| *F16K 15/14* | (2006.01) |
| *A61M 39/24* | (2006.01) |

(Continued)

(52) U.S. Cl.
CPC ............. *A61C 17/13* (2019.05); *A61C 17/04* (2013.01); *A61C 17/125* (2019.05); *A61M 1/0043* (2013.01); *A61M 39/24* (2013.01); *F16K 5/0407* (2013.01); *F16K 15/144* (2013.01); *F16K 15/16* (2013.01); *F16K 15/185* (2013.01);
(Continued)

(58) Field of Classification Search
CPC ...... F16K 15/144; F16K 15/16; F16K 15/181; F16K 15/185; F16K 15/188; F16K 5/0207; A61C 1/0061; A61C 17/04; A61C 17/06; A61C 17/096; A61C 17/12; A61C 17/125; A61C 17/13; A61M 39/24; A61M 2039/226; A61M 2039/244;
(Continued)

(56) References Cited

U.S. PATENT DOCUMENTS

| | | | | | |
|---|---|---|---|---|---|
| 1,528,703 | A | * | 3/1925 | Showers | ............... F16K 5/0207 137/269.5 |
| 3,474,818 | A | * | 10/1969 | Hartman | ................. F16K 5/045 137/269.5 |

(Continued)

*Primary Examiner* — Kenneth Rinehart
*Assistant Examiner* — Richard K. Durden
(74) *Attorney, Agent, or Firm* — David H. Chervitz

(57) ABSTRACT

A dental valve device has a valve body having a tip receiving end having a flexible tubing extending outwardly from the tip receiving end with the flexible tubing having a flexible tubing opening, a hose receiving end, a lumen formed between the flexible tubing opening and the hose receiving end, and a partial opening formed in the valve body, and a rotatable valve sealing body adapted to be inserted into the partial opening, the rotatable valve sealing body having a bore for alignment with the lumen formed between the flexible tubing opening and the hose receiving end, the bore having a tip receiving opening and a hose receiving opening.

20 Claims, 16 Drawing Sheets

Related U.S. Application Data is a continuation of application No. 14/925,749, filed on Oct. 28, 2015, now Pat. No. 10,010,712.

(51) Int. Cl.
| | |
|---|---|
| *A61M 1/00* | (2006.01) |
| *F16K 5/04* | (2006.01) |
| *F16K 15/16* | (2006.01) |
| *F16K 5/10* | (2006.01) |
| *A61M 39/22* | (2006.01) |
| *A61C 1/00* | (2006.01) |
| *A61C 17/08* | (2006.01) |

(52) U.S. Cl.
CPC .......... *F16K 15/188* (2013.01); *A61C 1/0061* (2013.01); *A61C 17/08* (2019.05); *A61M 2039/226* (2013.01); *A61M 2039/244* (2013.01); *A61M 2205/0205* (2013.01); *A61M 2205/0216* (2013.01); *F16K 5/10* (2013.01)

(58) Field of Classification Search
CPC ... Y10T 137/86944; F16L 27/04; F16L 37/52; F16L 47/18
USPC ....................................................... 285/261
See application file for complete search history.

(56) References Cited

U.S. PATENT DOCUMENTS

| | | | |
|---|---|---|---|
| 4,083,115 A * | 4/1978 | McKelvey | A61C 17/08 433/96 |
| 4,736,771 A * | 4/1988 | McCafferty | F16K 15/188 137/614.17 |
| 4,797,098 A | 1/1989 | Kawata | |
| 5,295,830 A * | 3/1994 | Shen | A61C 17/08 433/116 |
| 5,464,350 A | 11/1995 | Bierbaum | |
| 5,645,539 A * | 7/1997 | Solomon | A61M 39/0247 285/261 |
| 5,725,374 A | 3/1998 | Young | |
| 6,203,321 B1 * | 3/2001 | Helmer | A61C 17/04 433/95 |
| 6,602,072 B2 * | 8/2003 | Burney | A61C 17/08 433/96 |
| 8,192,421 B2 * | 6/2012 | Lopez | A61M 39/12 604/533 |
| 8,256,464 B2 | 9/2012 | Bushman et al. | |
| 8,763,638 B2 | 7/2014 | Deubler | |
| 9,277,978 B2 * | 3/2016 | Williams | A61C 17/04 |
| 9,333,061 B2 * | 5/2016 | Williams | A61C 17/04 |
| 9,693,842 B2 * | 7/2017 | Thomas | A61C 1/0061 |
| 9,907,632 B2 * | 3/2018 | Thomas | A61C 1/0061 |
| 10,010,712 B2 * | 7/2018 | Thomas | A61M 39/24 |
| 10,799,694 B2 * | 10/2020 | Thomas | A61M 39/24 |
| 2003/0219696 A1 | 11/2003 | Moreland | |
| 2008/0289696 A1 | 11/2008 | Bushman | |
| 2012/0305100 A1 | 12/2012 | Bushman et al. | |
| 2014/0017335 A1 * | 1/2014 | Dimov | C08K 5/0058 424/618 |
| 2014/0170595 A1 * | 6/2014 | Williams | A61C 17/04 433/95 |
| 2014/0239551 A1 * | 8/2014 | Williams | A61C 17/08 264/328.13 |
| 2020/0397532 A1 * | 12/2020 | Bushman | A61C 17/13 |

\* cited by examiner

DENTAL VALVE DEVICE HAVING A FLEXIBLE TUBING

RELATED APPLICATION

This application is a continuation-in-part of U.S. patent application Ser. No. 16/001,087, filed on Jun. 6, 2018, which was a continuation-in-part application of U.S. patent application Ser. No. 14/925,749, filed on Oct. 28, 2015, now U.S. Pat. No. 10,010,712, the disclosures of which are incorporated herein by reference.

BACKGROUND

This disclosure relates to a valve for a dental instrument for removing saliva and other fluids from a mouth of a patient and more particularly to a dental valve device having a flexible tubing. Further, the present disclosure relates to a dental valve device having a flexible tubing and having a check valve for preventing backflow of saliva, debris, and other fluids back into the mouth of the patient.

During a dental procedure it is important to be able to remove saliva, blood, water, tooth fragments, metals, and other debris or fluids from the mouth of a patient. Removal of this matter allows a dentist to be able to perform a procedure in an unobstructed manner. Various systems or devices have been developed to remove liquid and solid materials from a mouth during a dental procedure. One device that is capable of removing saliva is known as a saliva ejector or a low volume ejector. A saliva ejector typically comprises a plastic flexible tube for placement in the mouth of a patient. The saliva ejector tube is inserted into a valve which in turn is connected via suction tubing to a source of vacuum. In this manner, saliva is passed through the ejector tube, the valve, and the tubing to be disposed of in a sanitary manner. Once the procedure is completed, the ejector is removed from the valve and should be discarded and the valve should be sterilized by autoclaving to be used again. Although it is suggested to autoclave the valve after each use, it is known that autoclaving is hardly ever done. Another device that is capable of removing solid materials is a high volume evacuator system. A high volume evacuator system generally consists of a tube that may be inserted into a mouth of a patient with the tube inserted into a valve which is connected via a tubing to a source of vacuum. Again, in this manner, debris may be removed from the mouth of the patient. After the dental procedure, the tube is removed from the valve and disposed of and the valve should be sterilized for reuse. However, although it is suggested to sterilize the valve after use, it is known that this suggested procedure is hardly ever followed.

As can be appreciated, the saliva ejector and the high volume evacuator are used to remove liquids and debris from a mouth of a patient to prevent a patient from swallowing or aspirating liquids and debris produced during a dental procedure. Typically, when using these evacuator devices there is no backflow back into the mouth of a patient. However, there are times when backflow or a reverse flow may take place and previously removed liquids and debris may flow back into the mouth of the patient. It is also possible that if the systems are not properly maintained that fluids and debris from a previous patient may flow back into the mouth of a subsequent patient. These situations may be dangerous, are undesirable, and should be avoided.

In order to prevent backflow, there are various devices that are separate from the saliva ejector. These devices are inserted between the flexible tube and the dental valve or between the dental valve and suction tubing. These devices tend to be complex and expensive. Further, these devices have to be separately purchased, inventoried, and used apart from the flexible tube and the dental valve.

Therefore, it would be desirable to have dental valve device having a flexible tubing with the dental valve device and the flexible tubing being of unitary construction. It would also be advantageous to have a dental valve device having a flexible tubing and a check valve for preventing a backflow condition. It would also be desirable to have a dental valve having a flexible tubing and a check valve that is easy to install on or remove from suction tubing for a source of vacuum. Further, it would be advantageous to have a dental valve having a check valve and a flexible tubing that is disposable.

BRIEF SUMMARY

In one form of the present disclosure, a dental valve device is disclosed which comprises a valve body having a tip receiving end having a flexible tubing extending outwardly from the tip receiving end with the flexible tubing having a flexible tubing opening, a hose receiving end, a lumen formed between the flexible tubing opening and the hose receiving end, and a partial opening formed in the valve body, and a rotatable valve sealing body adapted to be inserted into the partial opening, the rotatable valve sealing body having a bore for alignment with the lumen formed between the flexible tubing opening and the hose receiving end, the bore having a tip receiving opening and a hose receiving opening.

In another form of the present disclosure, a dental valve device comprises a valve body having a tip receiving end having a flexible tubing extending outwardly from the tip receiving end with the flexible tubing having a flexible tubing opening, an exterior rib, a tip receiving end, a hose receiving end, a lumen formed between the tip receiving end and the hose receiving end, a partial opening formed in the valve body and a rotatable valve sealing body adapted to being inserted into the partial opening, the rotatable valve sealing body having a bore for alignment with the lumen formed between the tip receiving end and the hose receiving end, the bore having a tip receiving opening and a hose receiving opening, and the rotatable valve sealing body having a check valve positioned in the bore.

In yet another form of the present disclosure, a dental valve device kit comprises a valve body having a tip receiving end having a flexible tubing extending outwardly from the tip receiving end with the flexible tubing having a flexible tubing opening, a hose receiving end, a lumen formed between the flexible tubing opening and the hose receiving end, and a partial opening formed in the valve body, a rotatable valve sealing body adapted to be inserted into the partial opening, the rotatable valve sealing body having a bore for alignment with the lumen formed between the flexible tubing opening and the hose receiving end, the bore having a tip receiving opening and a hose receiving opening, and a cap device for insertion into a hose connected to a source of vacuum.

The present disclosure provides a dental valve device having a flexible tubing that is suitable for one time use and may be discarded after a single use.

The present disclosure is also directed to a dental valve device having a flexible tubing and a check valve that is suitable for one time use and may be discarded after a single use.

The present disclosure provides a dental valve device having a flexible tubing with the flexible tubing for being placed in a mouth of a patient during a dental procedure.

The present disclosure provides a dental valve device having a flexible tubing and a check valve with the flexible tubing being adapted for placement in a mouth of a patient during a dental procedure.

The present disclosure provides a dental valve device having a flexible tubing a check valve that is easy to install on suction tubing connected to a source of vacuum.

The present disclosure also provides a dental valve device having a flexible tubing and a check valve that is easy to install on suction tubing connected to a source of vacuum.

The present disclosure provides a dental valve device having a flexible tubing that is small, lightweight, easy to handle, easy to install, and easy to operate.

The present disclosure is also directed to a dental valve device having a flexible tubing and a check valve that is small, lightweight, easy to handle, easy to install, and easy to operate.

The present disclosure also provides a dental valve device having a flexible tubing which is of simple construction and design and which can be easily employed with highly reliable results.

The present disclosure also provides a dental valve device having a flexible tubing and a check valve which is of simple construction and design and which can be easily employed with highly reliable results.

The present disclosure is related to a dental valve device having a flexible tubing and a check valve that does not require sterilization and prevents against any backflow and cross-contamination.

The present disclosure provides a dental valve device having a flexible tubing that may have an antimicrobial agent or chemical incorporated into the device to prevent any bacterial growth on the device. The antimicrobial agent or chemical may also be a coating applied to the dental valve device having a flexible tubing.

The present disclosure provides a dental valve device having a flexible tubing and a check valve that may have an antimicrobial agent or chemical incorporated into the device to prevent any bacterial growth on the device. The antimicrobial agent or chemical may also be a coating applied to the dental valve device.

The present disclosure is related to a dental valve device having a flexible tubing that may be constructed of plastic that is recyclable or biodegradable to reduce the cost of the device and to allow the device to be discarded after a single use.

The present disclosure is related to a dental valve device having a flexible tubing and a check valve that may be constructed of plastic that is recyclable or biodegradable to reduce the cost of the device and to allow the device to be discarded after a single use.

The present disclosure provides a dental valve device having a flexible tubing that further includes a cap device that may be used to cap off a suction tubing connected to a source of vacuum when the dental valve device having a flexible tubing is removed from the suction tubing connected to the source of vacuum to reduce or eliminate any sound or noise associated with the source of vacuum.

The present disclosure provides a dental valve device having a flexible tubing and a check valve that further includes a cap device that may be used to cap off a suction tubing connected to a source of vacuum when the dental valve device is removed from the suction tubing connected to the source of vacuum to reduce or eliminate any sound or noise associated with the source of vacuum.

The present disclosure is further directed to a dental valve device having a flexible tubing that has a rotatable valve sealing body that is easy to manipulate during a dental operation to open or close the valve.

The present disclosure is related to a dental valve device having a flexible tubing and a check valve that has a rotatable valve sealing body that is easy to manipulate during a dental operation to open or close the valve and also incorporates a check valve to automatically prevent backflow of saliva, liquid, or other material.

These and other advantages of the present disclosure will become apparent after considering the following detailed specification in conjunction with the accompanying drawings, wherein:

DETAILED DESCRIPTION OF A PREFERRED EMBODIMENT

Figure 1:
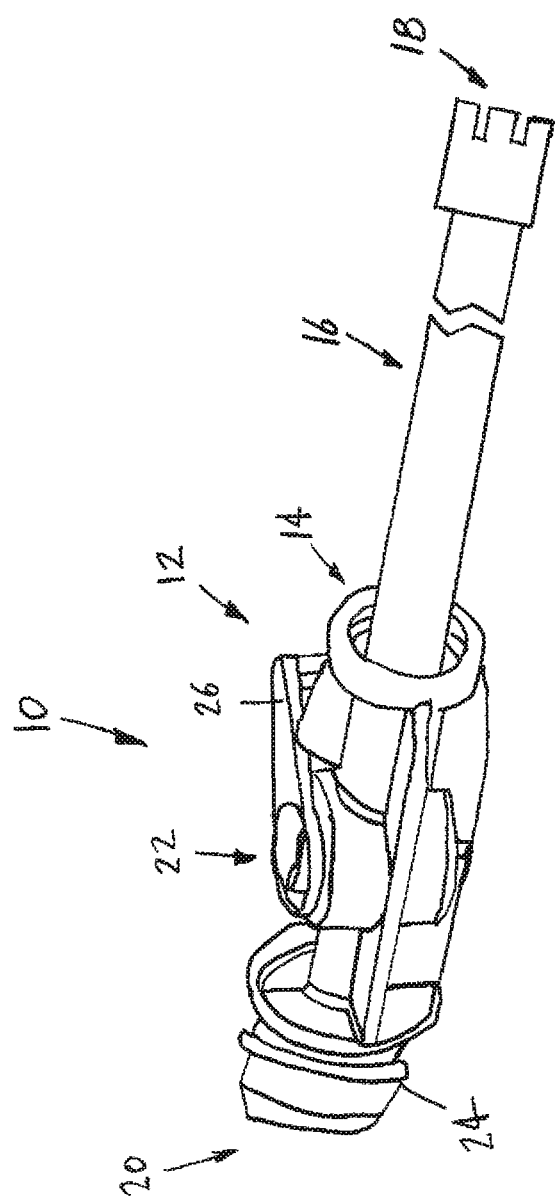
FIG. 1 is a perspective view of a dental valve device having a flexible tubing constructed according to the present disclosure.

Referring now to the drawings, wherein like numbers refer to like items, number 10 identifies a dental valve device for use with a dental system (not shown) constructed according to the present disclosure. With reference now to FIG. 1, the valve 10 comprises a valve body 12 having a tip receiving end 14 having a flexible tubing 16 extending outwardly from the tip receiving end 14 with the flexible tubing 16 having a flexible tubing opening 18, a suction tubing or hose receiving end 20, and a rotatable valve sealing body 22. The tip receiving end 14 has the flexible tubing 16 incorporated therein which negates having to have a supply of evacuator tip devices (not shown) such as a high volume evacuator or a low volume evacuator (saliva ejector). By way of example only, the valve body 12 and the flexible tubing 16 may be formed by over molding the flexible tubing 16 onto an existing mold for the valve body 12 or by using a 2-shot mold in which the flexible tubing 16 is formed by a first plastic shot to generate the tubing 16 and a second shot generates the body 12 grafted to the tubing 16. The tubing 16 may be attached to the body 12 by ultrasonically welding, heat welding, or by using an adhesive or a primer and an adhesive. The hose receiving end 20 is adapted to receive a vacuum line or a hose (not shown) which is connected to a suction system (also not shown) which is used to dispose of any saliva, liquid, or debris removed from a mouth of a patient. The hose receiving end 20 also has a circumferential channel 24 that is adapted to accept an O-ring (not shown). The O-ring is used to further secure a hose or a tailpiece (not shown) to the hose receiving end 20. It is also possible that the hose receiving end 20 may incorporate a structure to secure a hose to the end 20 without the use of the channel 24 or the requirement for an O-ring. For example, the end 20 may be barbed so that the barbs may hold a hose thereon. The device 10 is constructed of material that allows the device 10 to be disposable and suitable for one time use. The device 10 also has a handle 26 as part of the rotatable valve sealing body 22 for manual operation of the rotatable valve sealing body 22. Manual operation of the handle 26 will open the device 10, close the device 10, or partially open the device 10, as will be discussed more fully herein. As can be appreciated, a suction system provides suction through the flexible tube opening 18, the flexible tubing 16, the device 10, and a hose so that any debris, liquid, or saliva that is introduced into the flexible tube opening 18 is removed through the valve 10, and a hose when the rotatable valve sealing body 22 of the device 10 is in an open state or a partially open state.

Figure 2:
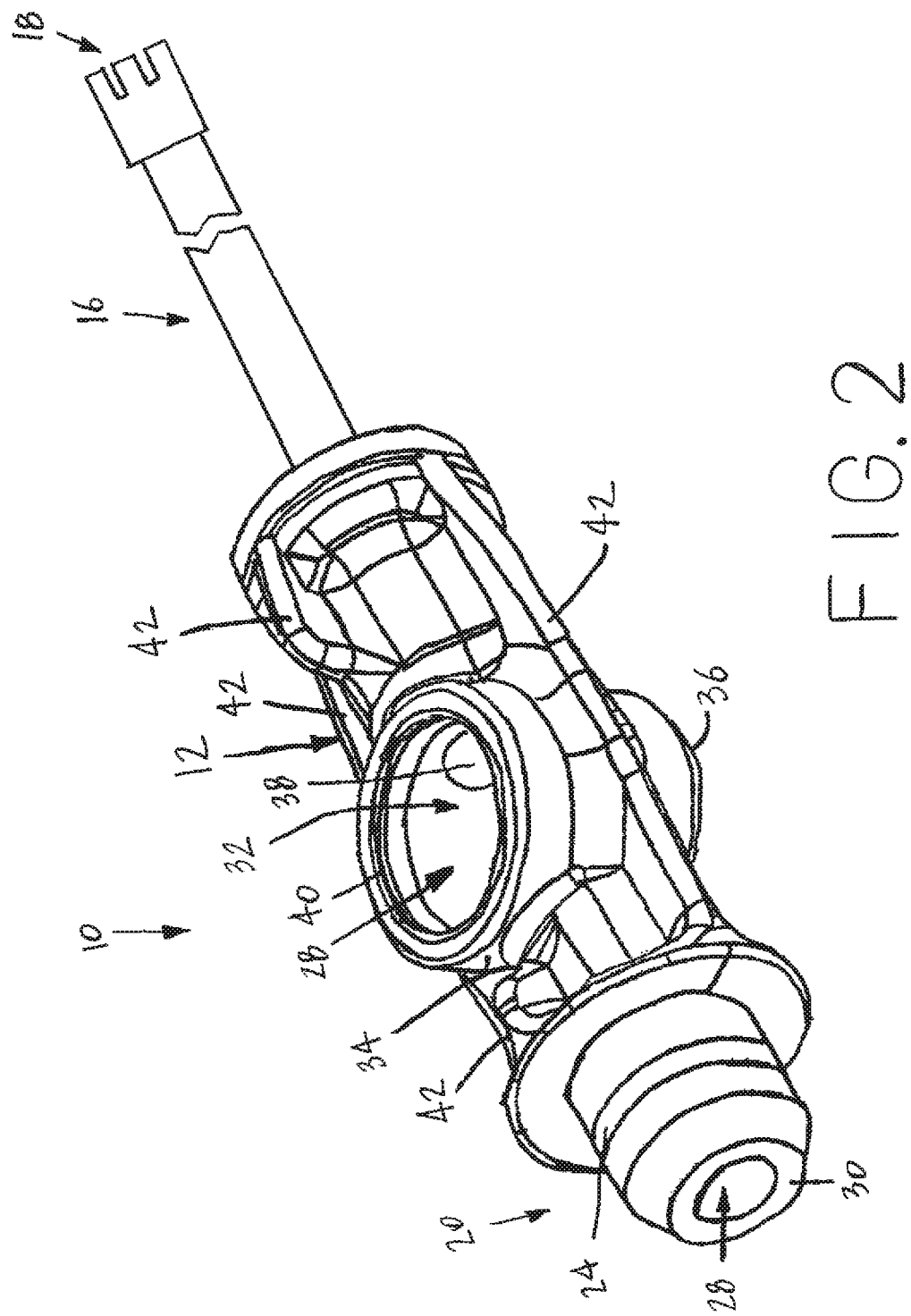
FIG. 2 is a perspective view of a dental valve device having a flexible tubing constructed according to the present disclosure with a valve sealing body removed.

With reference now to FIG. 2, the device 10 is shown with the rotatable valve sealing body 22 being removed for clarity. The valve body 12 has a lumen 28 and an opening 30 at the hose receiving end 20. The lumen 28 continues through the valve body 12 to the flexible tubing opening 18 of the flexible tubing 16. The valve body 12 also has a partial opening 32 formed on a top side 34 of the valve body 12. The partial opening 32 does not go all the way through the valve body 12. The partial opening 32 is blocked by a bottom 36 of the valve body 12. An opening 38 is also shown in the lumen 28 between the flexible tubing opening 18 and the partial opening 32. An annular channel or ring 40 is formed in the partial opening 32 which is used to retain the rotatable valve sealing body 22 in place, as will be explained in further detail herein. Although the channel 40 is disclosed, it is also possible and contemplated that the valve body 12 and/or the valve sealing body 22 may be constructed so that there is a frictional engagement between the valve body 12 and the sealing body 22 to hold the sealing body 22 within the valve body 12. The valve body 12 also has a number of exterior ribs 42 that add strength to the valve body 12 and also assist in forming the valve body 12.

In operation of the device 10, the hose receiving end 20 of the device 10 is placed on to a hose connected to a suction system and the flexible tubing 16 may be placed in a mouth of a dental patient. The handle 26, which may include an indicator to indicate the closed position and the open position, is manually operated to open the device 10. Once in the open position, air is allowed to flow through the flexible tubing opening 18, the flexible tubing 16, the lumen 28, the rotatable valve sealing body 22, the hose receiving end 20 and into a suction system. When suction is not needed during a dental procedure, the handle 26 is moved to the closed position. Further, once a dental procedure has been completed, the handle 26 is moved to the closed position, the device 10 is easily separated from the hose. Once the device 10 is disconnected from the hose, the device 10 may be disposed of by any suitable manner. A new device 10 is then connected to the hose to begin another dental procedure.

Figure 3:
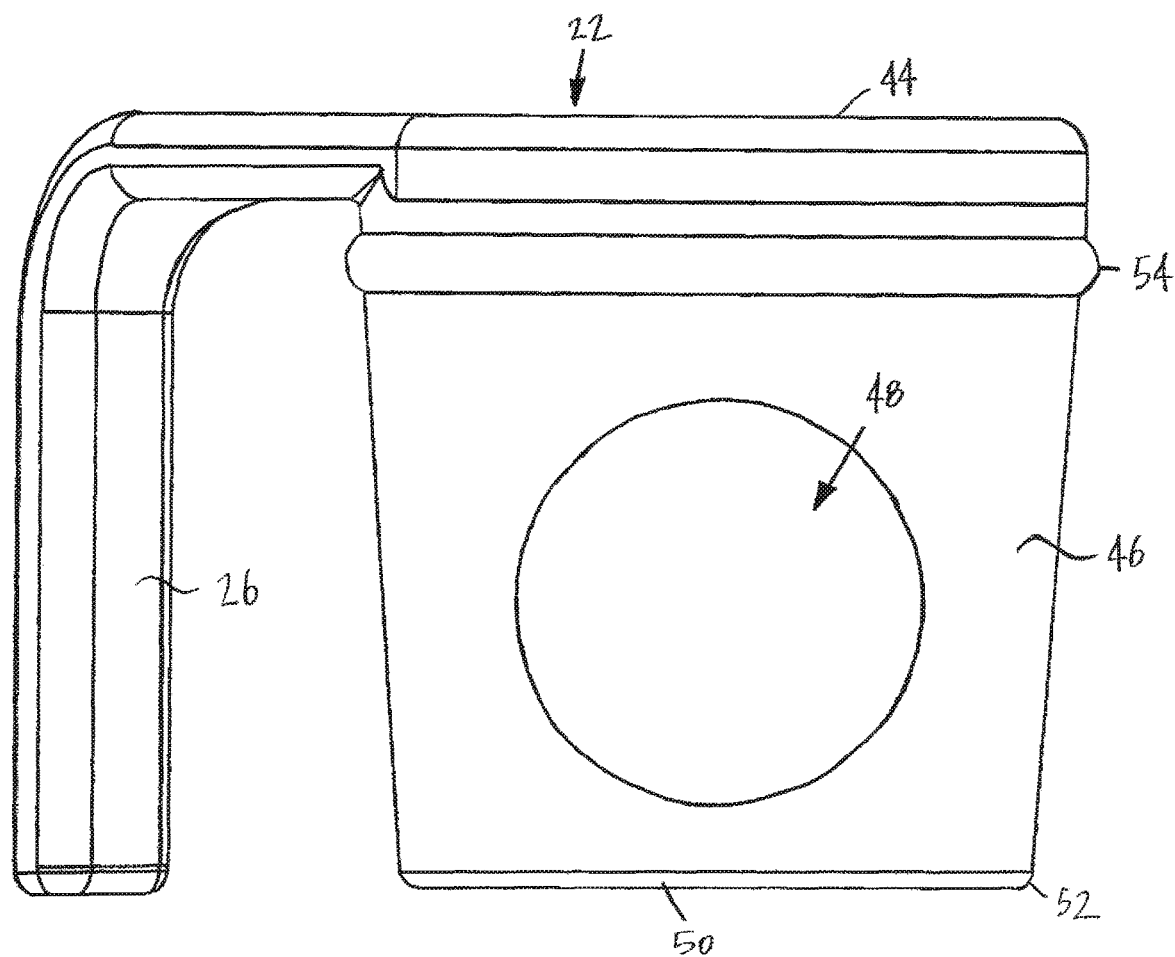
FIG. 3 is side perspective view of a valve sealing body constructed according to the present disclosure.

FIG. 3 shows the rotatable valve sealing body 22 being removed from the valve body 12. The rotatable valve sealing body 22 has a top 44, a central body portion 46 having a bore 48, and a bottom 50. The bottom 50 may have a chamfered or bevel section 52 which aids in inserting the valve sealing body 22 into the partial opening 32 (FIG. 2) of the valve body 12. The handle 26 may be formed to be part of the top 44. The central body portion 46 also has an annular ridge portion 54 near the top 44. The ridge portion 54 is capable of fitting into the ring 40 (FIG. 2) in a snap fit engagement to secure the rotatable valve sealing body 22 within the valve body 12. The bore 48 is adapted to be aligned with the lumen 28 of the valve body 12. When the bore 48 is aligned with the lumen 28, the device 10 is in an opened position and the source of vacuum will draw any fluid or debris from the flexible tubing opening 18 through the lumen 28 and the bore 48 and out through the hose receiving end 16. In this manner, fluid and debris may be removed from a mouth during a dental procedure or operation. Although the ridge 54 is shown, it is possible that an annular ring may be formed in the central body portion 46 and an O-ring may be used to hold the valve sealing body 22 in place. Also, although one ridge 54 is depicted, it is contemplated that another ridge 54 may be formed on the central body portion 46 near the bottom 50 and another ring 40 may be formed in the opening 32 near the bottom 36 to receive a second ridge 54 to further secure the valve sealing body 22 in place.

Figure 4:
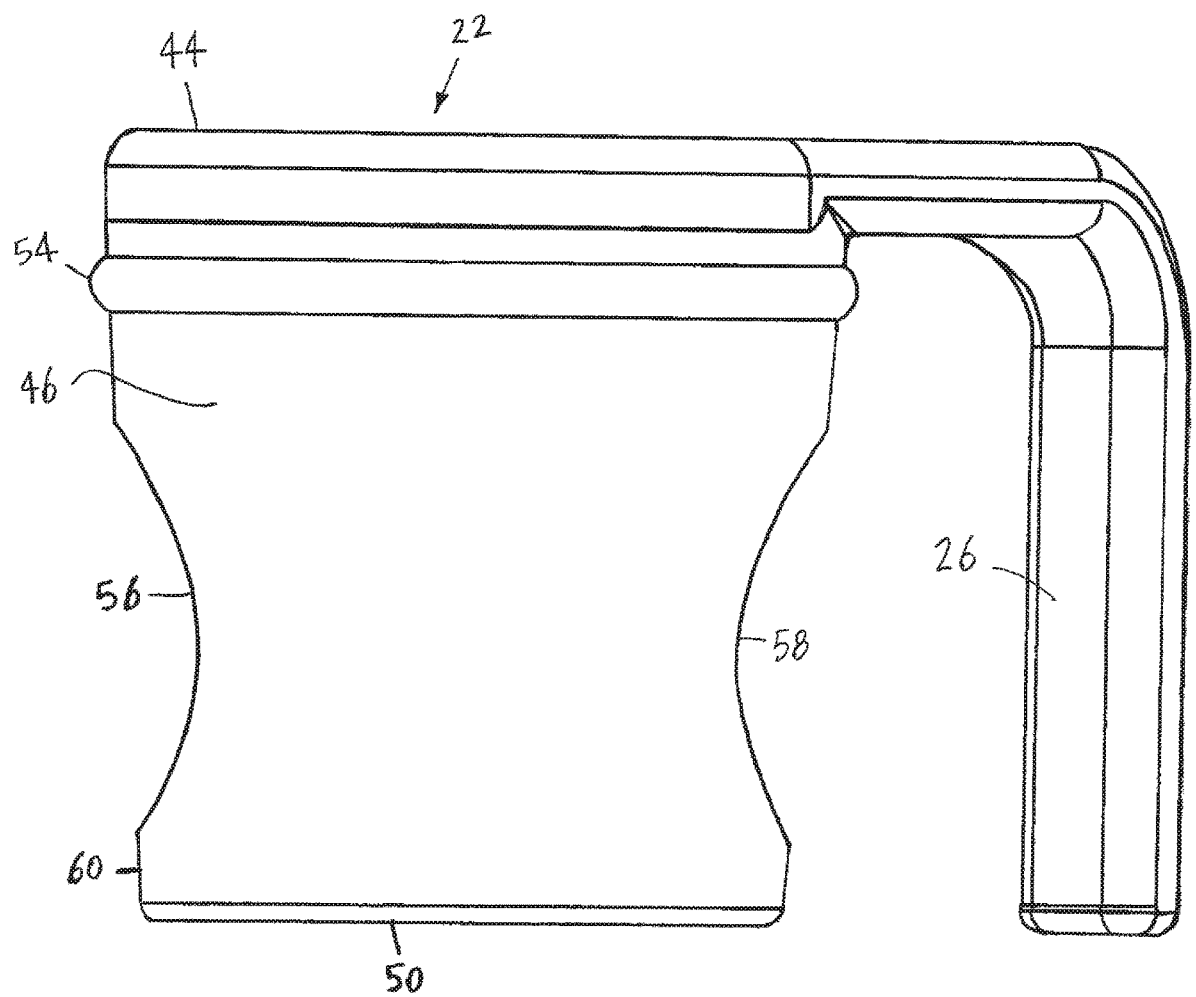
FIG. 4 is another side perspective view of the valve sealing body shown in FIG. 3.

Referring now to FIG. 4, another side perspective view of the rotatable valve sealing body 22 being removed from the valve body 12 is illustrated. The rotatable valve sealing body 22 has the top 44, the central body portion 46 having a first opening 56 and a second opening 58, and the bottom 50. The openings 56 and 58 are aligned with the bore 48 (FIG. 3). When the rotatable valve sealing body 22 is in a closed position, the central body portion 46 will block any air flow through the valve body 12. In essence, the bore 48 is no longer aligned with the lumen 28 formed in the valve body 12. The rotatable valve sealing body 22 is moved into the closed position by use of the handle 26. The openings 56 and 58 are concave and this provides a lower annular ring 60 that is formed in the sealing body 22. The lower annular ring 60 is employed to provide a frictional engagement between the ring 60 and the partial opening 32.

Figure 5:
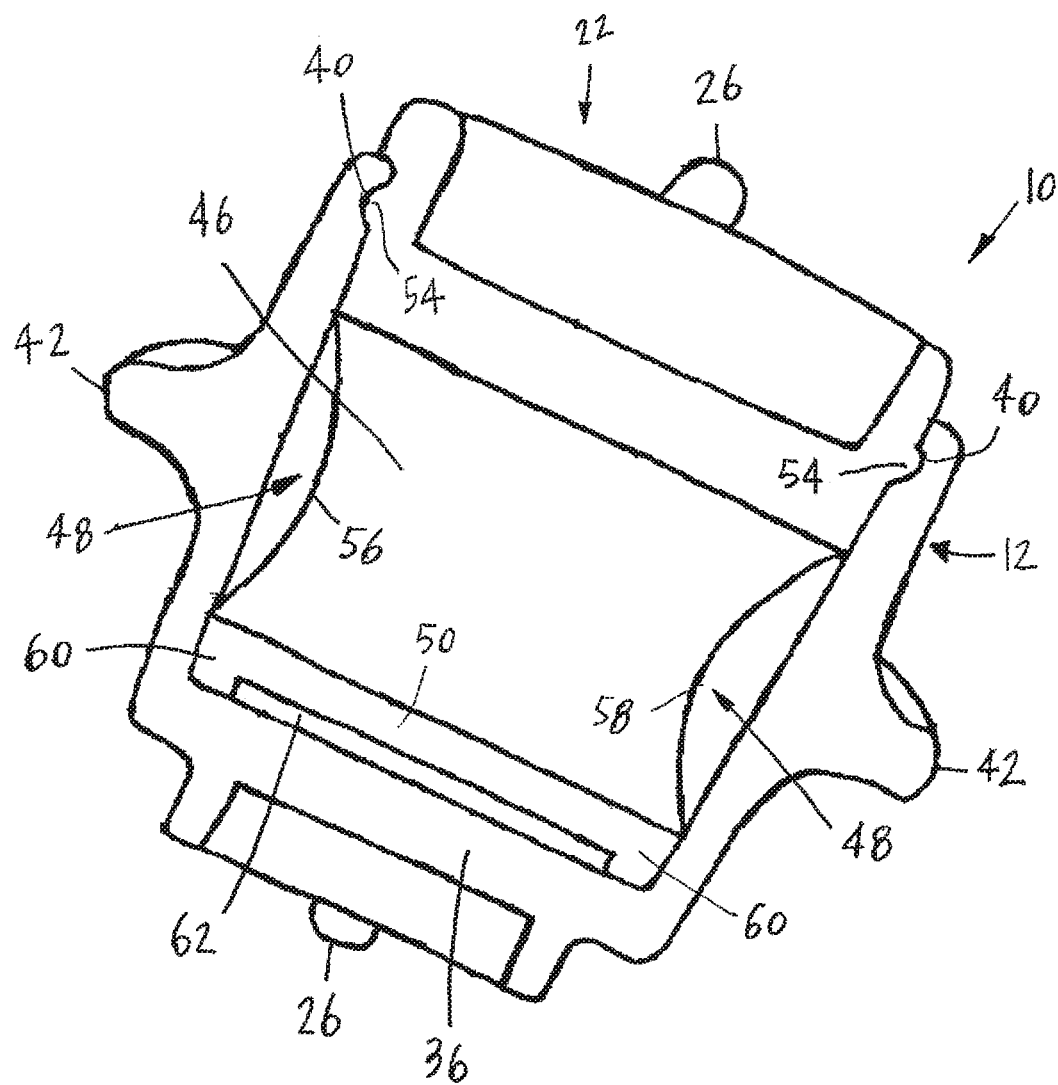
FIG. 5 is a cross-sectional view of the dental valve device.

FIG. 5 is a cross-sectional view of the dental valve device 10 with the rotatable valve sealing body 22 in the closed position. The device 10 has the valve body 12 having the rotatable valve sealing body 22 mounted therein. The rotatable valve sealing body 22 is held in place by use of the ridge 54 being snapped into place within the ring 40. The bottom 50 of the rotatable valve sealing body 22 is adjacent to the bottom 36 of the valve body 12. In this manner, the rotatable valve sealing body 22 is able to rotate within the valve body 12. Further, the bottom 36 ensures that the partial opening 32 (FIG. 2) is a partial opening and the opening 32 does not go all the way through the valve body 12. The opening 32 reduces the risk that the rotatable valve sealing body 22 will become disengaged during use or that the dental valve device 10 will fail during use. The rotatable valve sealing body 22 also has the bore 48 formed therein between the openings 56 and 58. The central portion 46 of the valve sealing body 22 inhibits any air flow through the valve body 12. As previously described, the openings 56 and 58 are concave and the sealing body 22 has the lower annular ring 60 that is in frictional engagement with the partial opening 32 near the bottom 36. The bottom 50 has a central indentation 62 formed within the annular ring 60 to provide smooth rotation of the valve sealing body 22 within the partial opening 32. The valve body 12 also has the exterior ribs 42 that add strength to the valve body 12 and also assist in forming the valve body 12. The handle 26 is also shown as being part of the device 10.

Figure 6:
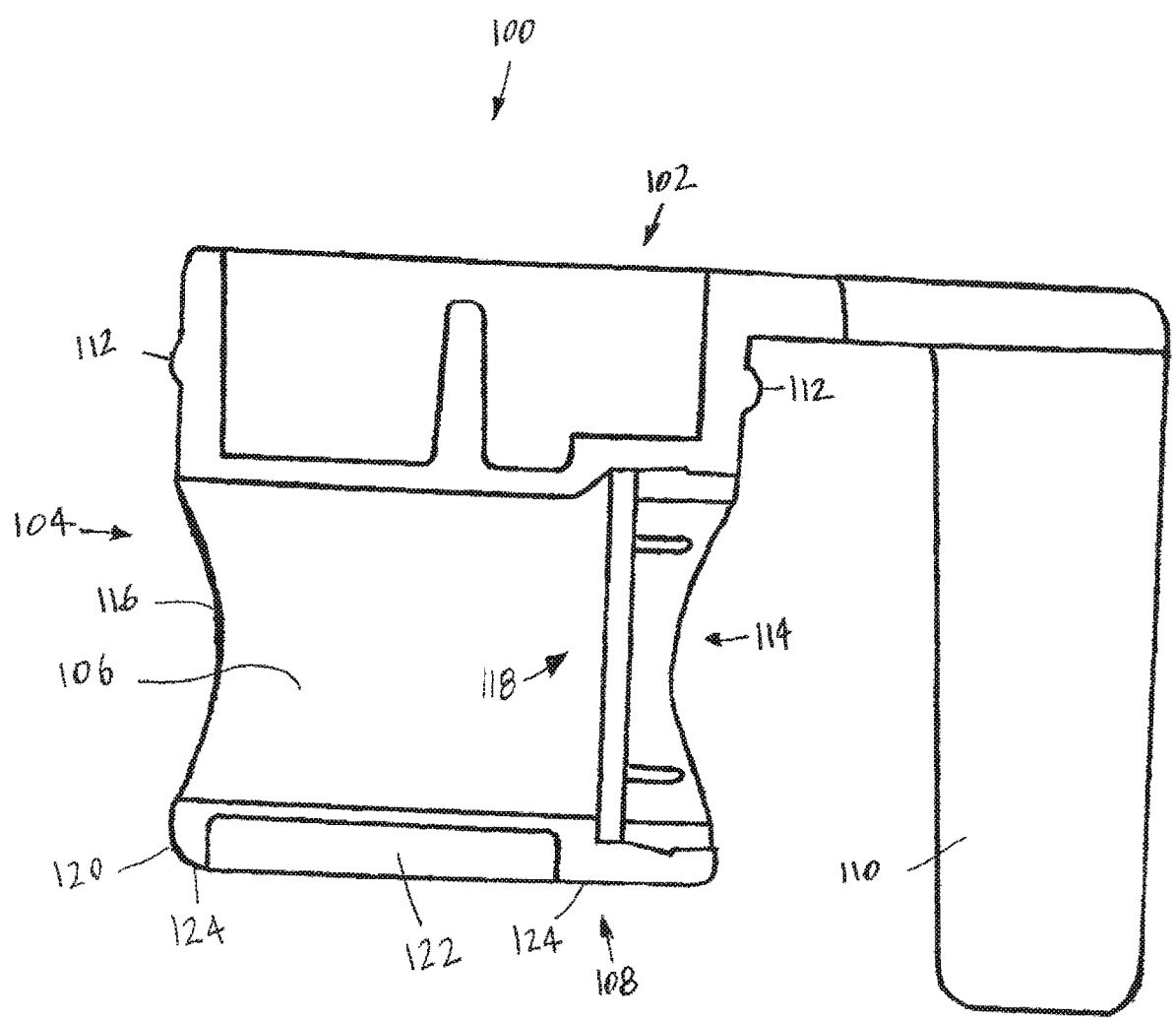
FIG. 6 is a cross-sectional view of another embodiment of a valve sealing body constructed according to the present disclosure with a check valve in a closed position.

FIG. 6 shows a cross-sectional view of another embodiment of a rotatable valve sealing body 100 with the body 100 having been removed from the valve body 12. The rotatable valve sealing body 100 has a top 102, a central body portion 104 having a bore 106, and a bottom 108. A handle 110 is part of the top 102. The central body portion 104 also has an annular ridge portion 112 near the top 102. The ridge portion 112 is capable of fitting into the ring 40 (FIG. 2) in a snap fit engagement to secure the rotatable valve sealing body 100 within the valve body 12. The bore 106 is adapted to be aligned with the lumen 28 of the valve body 12. The bore 106 of the rotatable valve sealing body 100 also has a first opening 114 and a second opening 116. The first opening 114 is used to be aligned with the opening 38 (FIG. 1) in the valve body 12. The second opening 116 is used to be aligned with the opening 30 (FIG. 2) at the hose receiving end 20 of the valve body 12. The first opening 114 has a check valve 118 positioned therein to selectively open or close the first opening 114. The check valve 118 is provided for allowing liquid, saliva, or debris to pass from the flexible tubing opening 18, the check valve 118, the bore 106, the second opening 116, and out the hose receiving end 20 when the check valve 118 is opened. However, the check valve 118 also prevents any liquid, saliva, or debris from passing or traveling from the hose receiving end 20, the second opening 116, the bore 106, and through the check valve 118 when the check valve 118 is closed. The check valve 118 will close when a reduced pressure occurs from an interaction of a mouth of a patient on the flexible tubing 16. For example, a patient may be requested to close the mouth of the patient around the flexible tubing 16. When this occurs, a reduced pressure results in which a backflow may occur. The check valve 118 is sensitive to this pressure differential and will close to prevent backflow. The check valve 118 is shown in the closed position in FIG. 6.

As can be appreciated, when the bore 106 is aligned with the lumen 28, the device 100 is in an opened position and the source of vacuum will draw any fluid, saliva, or debris from the flexible tubing opening 18 through the lumen 28 and the bore 106 and out through the hose receiving end 20. The check valve 118 is in an opened position or configuration at this particular time. In this manner, fluid, saliva, and debris may be removed from a mouth of a patient during a dental procedure or operation. Although the ridge 112 is shown, it is possible that an annular ring may be formed in the central body portion 104 and an O-ring may be used to hold the valve sealing body 100 in place. Also, although one ridge 112 is depicted, it is contemplated that another ridge 112 may be formed on the central body portion 104 near the bottom 108 and another ring 40 may be formed in the partial opening 32 (FIG. 2) near the bottom 36 (FIG. 2) to receive the other ridge 112 to further secure the valve sealing body 100 in place.

The rotatable valve sealing body 100 also has an annular ring 120 formed in the bottom 108. A central indentation 122 is formed within the annular ring 120. The annular ring 120 has a surface 124 that contacts an interior surface (not shown) of the bottom 36 of the valve body 12. The annular ring 120, the central indentation 122, and the surface 124 facilitate smooth and easy rotation of the rotatable valve sealing body 100 within the valve body 12. The annular ring 120, the central indentation 122, and the surface 124 further allow rotation of the body 100 without being bound up within the valve body 12.

Figure 7:
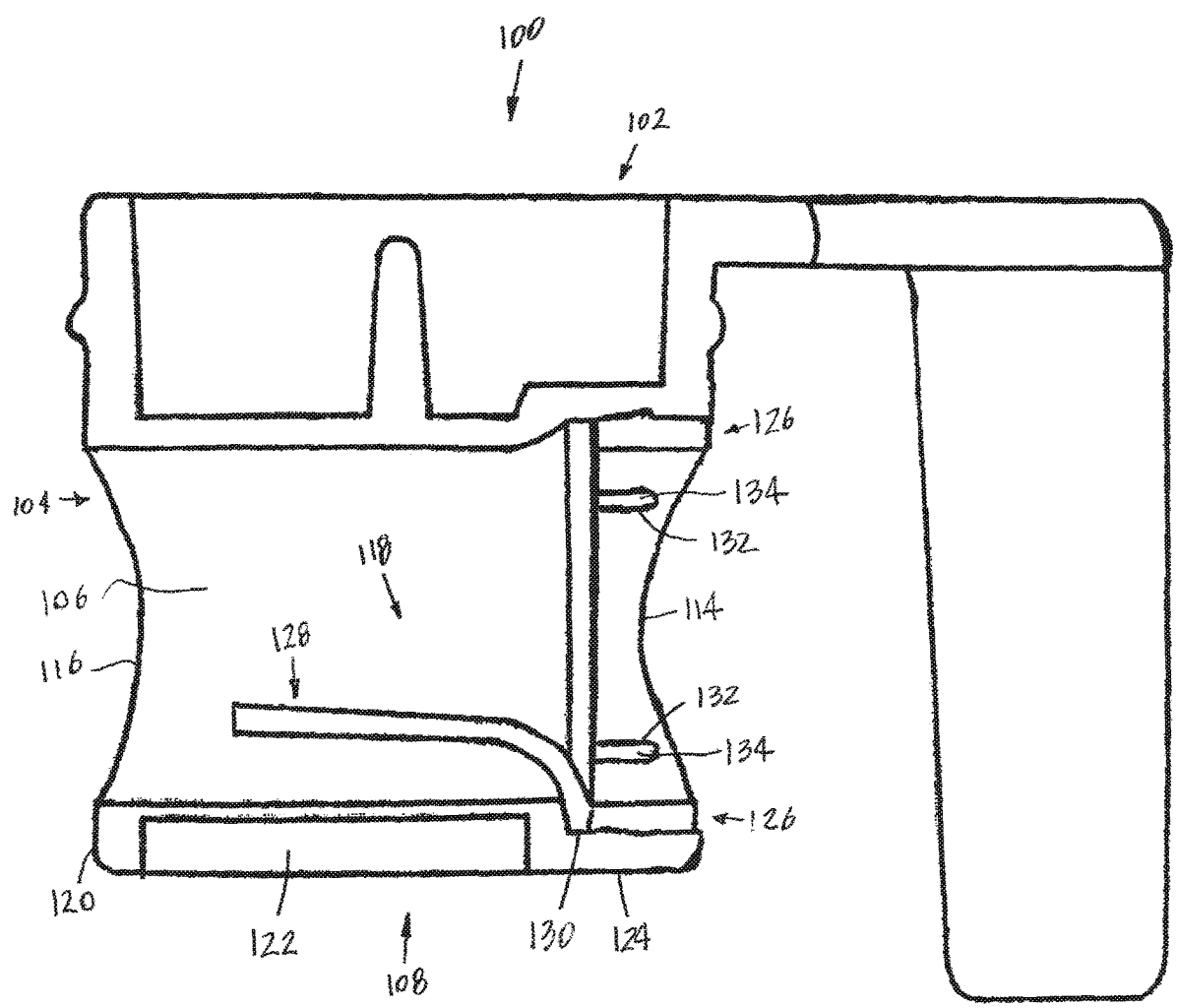
FIG. 7 is a cross-sectional view of the valve sealing body shown in FIG. 6 with a check valve an opened position.

Referring now to FIG. 7, the check valve 118 of the rotatable valve sealing body 100 is illustrated in the opened position. The check valve 118 comprises a housing 126 having a flap portion 128 being connected at an end portion 130. The connection of the flap portion 128 at the end portion 130 allows the check valve 118 to opened or closed. The end portion 130 may be a hinge device that allows the flap portion 128 to move relative to the housing 126. The housing 126 also has retaining rib openings 132 formed in the housing 126. The rotatable valve sealing body 110 has retaining ribs 134 formed in the first opening 114. The openings 132 are used to receive the ribs 134 therein for retaining the check valve 118 in the first opening 114. In this manner, a snap fit engagement of the check valve 118 within the first opening 114 is provided. Although the openings 132 and the ribs 134 are shown, it is possible that other retention or engagement type constructions are contemplated, such as using an adhesive or forming the check valve 118 and the body 100 as a unitary piece or construction. As can be appreciated, when the flap portion 128 is in the opened position the flap portion 128 will only be within the bore 106 of the body 100. The rotatable valve sealing body 100 is also shown having the top 102, the central body portion 104 having the first opening 114 and the second opening 116, the bottom 108, the annular ring 120, the central indentation 122, and the surface 124. The openings 114 and 116 are concave and this provides for smooth rotation of the body 100 within the valve body 12.

Figure 8:
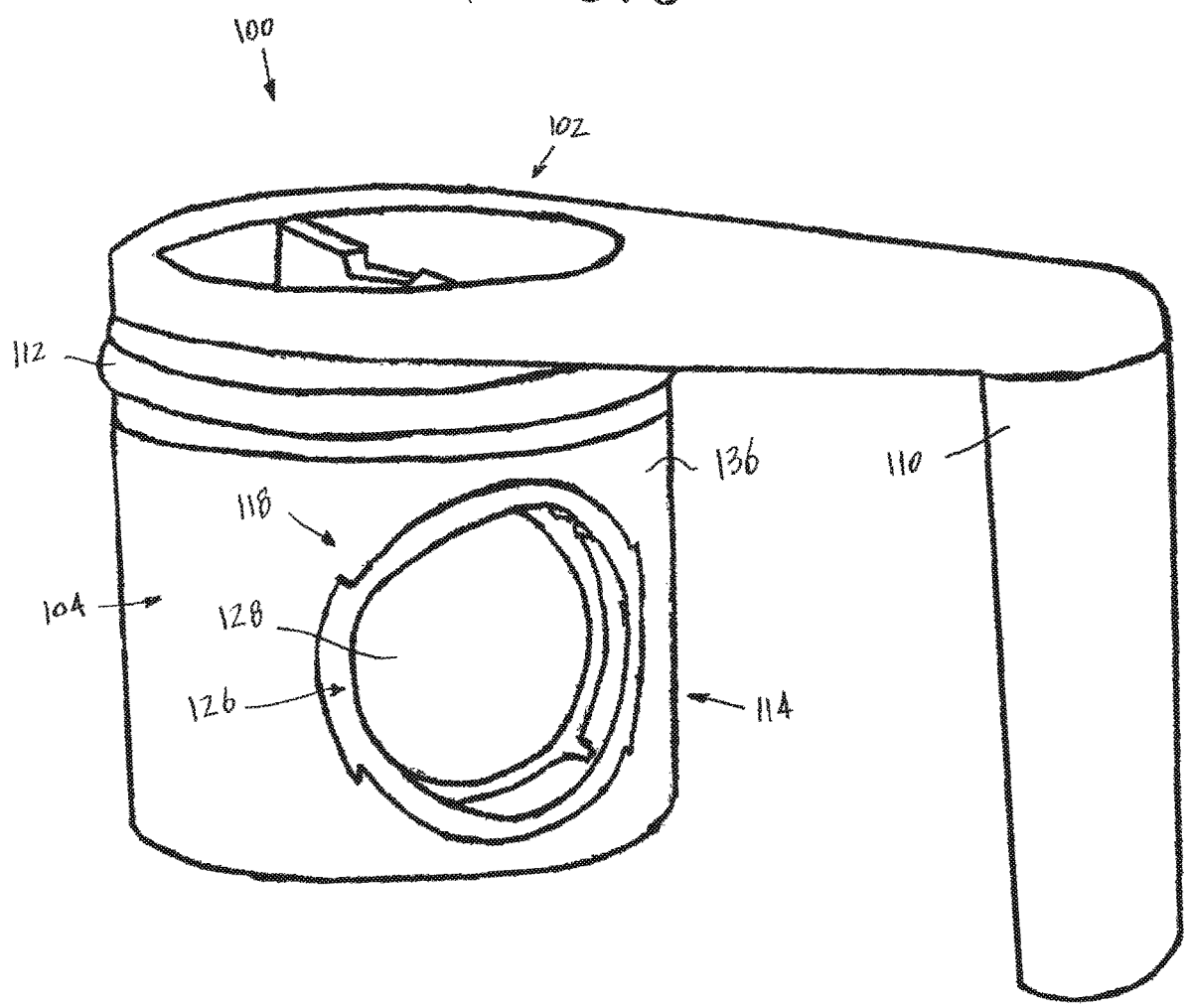
FIG. 8 is a perspective view of the valve seal body of FIG. 6 constructed according to the present disclosure with the check valve shown in the closed position.

FIG. 8 shows a perspective view of the rotatable valve sealing body 100 with the check valve 118 in the closed position. The housing 126 is positioned in or on the first opening 114. The flap portion 128 is positioned up against the housing 126. With the flap portion 128 in this position, the closed position, no fluid, saliva, or debris will flow through the body 100. The body 100 has the central body portion 104 having an exterior surface 136. The annular ridge portion 112 is positioned near the top 102. Also, the handle 110 is part of the top 102.

Figure 9:
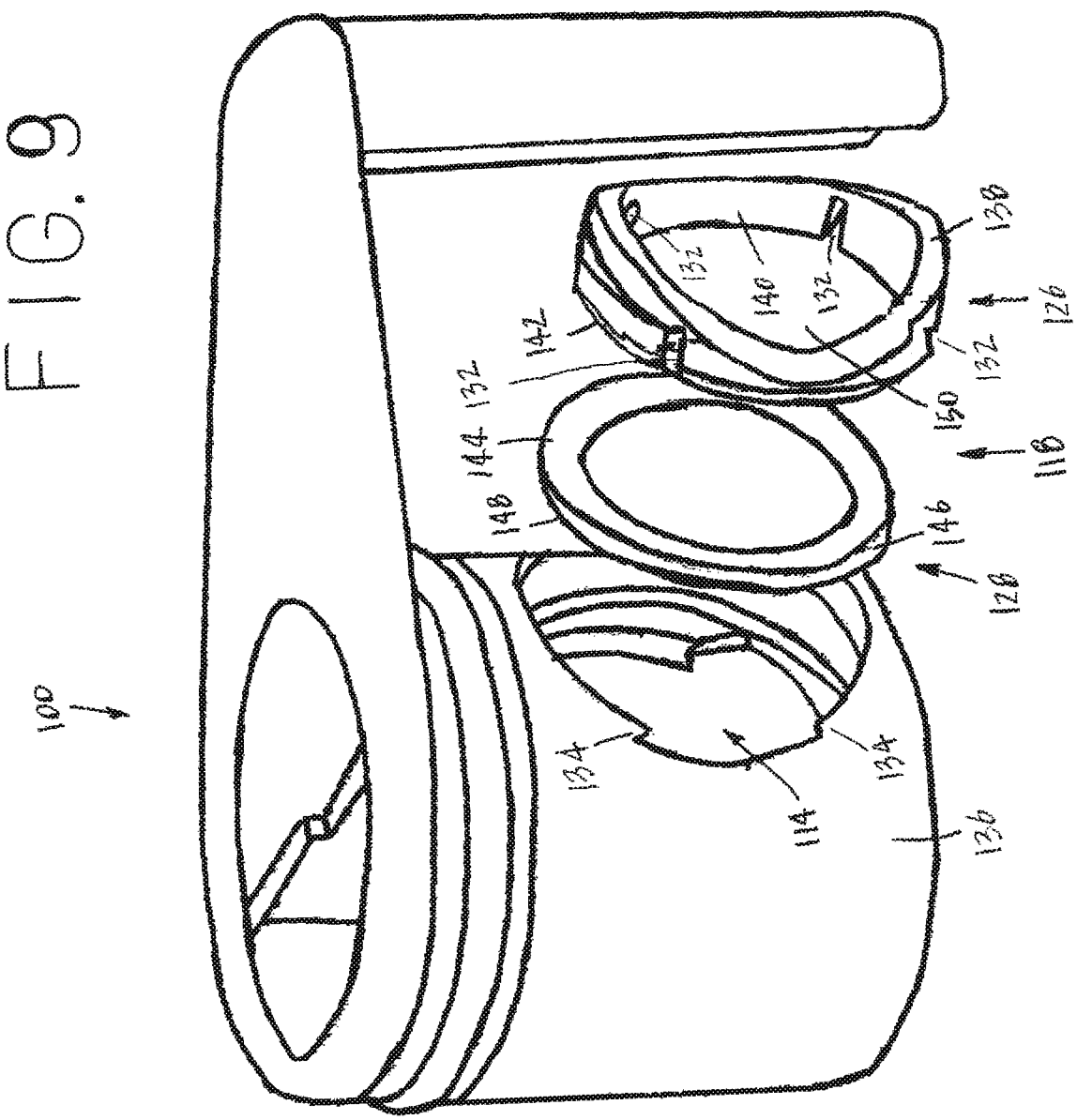
FIG. 9 is a perspective view of the valve seal body of FIG. 6 constructed according to the present disclosure with the check valve removed from the valve seal body and shown in an exploded view.

With reference now to FIG. 9, a perspective view of the rotatable valve sealing body 100 is shown with the check valve 118 removed from the first opening 114. The check valve 118 is also depicted in an exploded view in that the housing 126 and the flap portion 128 have been separated. As has been discussed, the housing 126 and the flap portion 128 may be a unitary construction. The housing 126 has a front surface 138 that is concave to follow the concave first opening 114 so that the front surface 138 is flush with the exterior surface 136 when the housing 126 is inserted into the first opening 114, as is depicted in FIG. 8. The housing 126 also has a center portion 140 and a back 142. The center portion 140 and the back 142 have the openings 132 formed therein. Although four openings 132 are shown, it is contemplated that more or less openings 132 may be provided in the housing 126. The flap portion 128 has a front side 144, a center portion 146, and a back side 148. The front side 144 and the center portion 146 are sized and shaped to fit over the center portion 140 and the back 142 of the housing 126. As can be appreciated, the flap portion 128 is a solid piece and the housing 126 has a central opening 150. The flap portion 128 is used to cover or close the central opening 150. It is also possible that the back 142 of the housing 126 may have a recess, groove, or rabbet formed therein to receive or seat the flap portion 128 therein. The flap portion 128 may be connected to the housing 126 in any suitable manner. The first opening 114 has the ribs 134 that are used to capture the openings 132 to hold the housing 126 in place in or around the first opening 114. Although two of the four ribs 134 are depicted, as with the openings 132, more or less ribs 134 are possible and contemplated.

Figure 10:
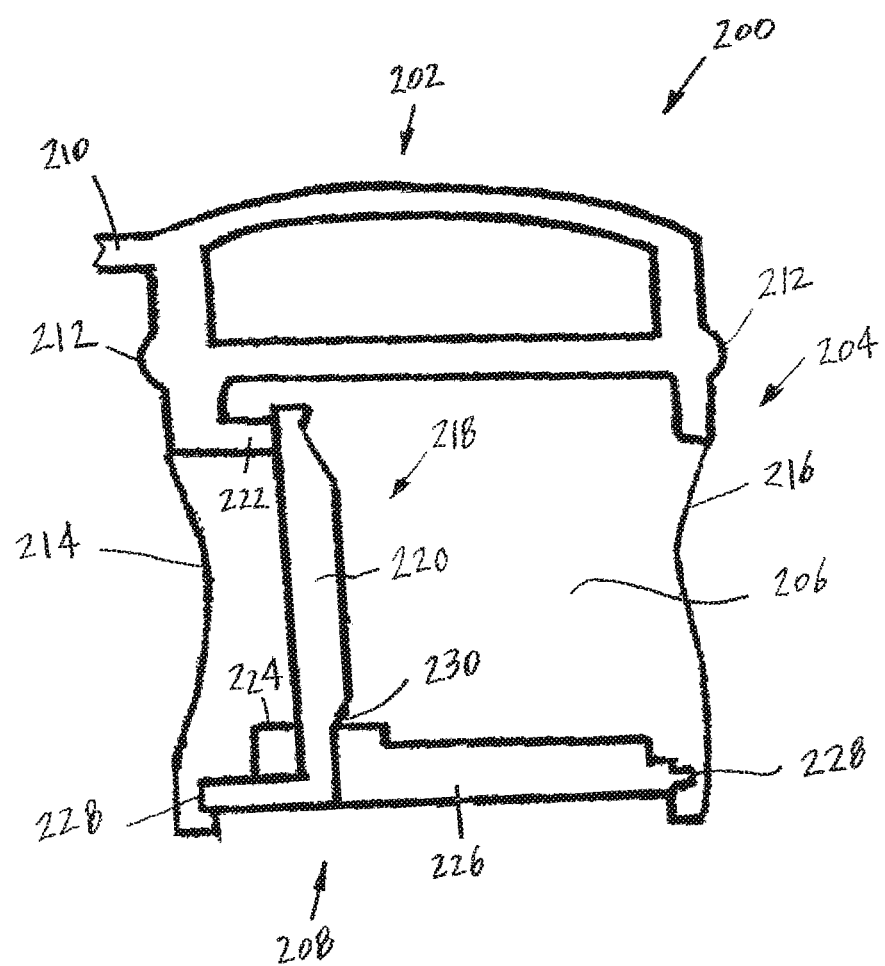
FIG. 10 is a partial cross-sectional view of another embodiment of a valve sealing device having a check valve shown in a closed position constructed according to the present disclosure.
Figure 11:
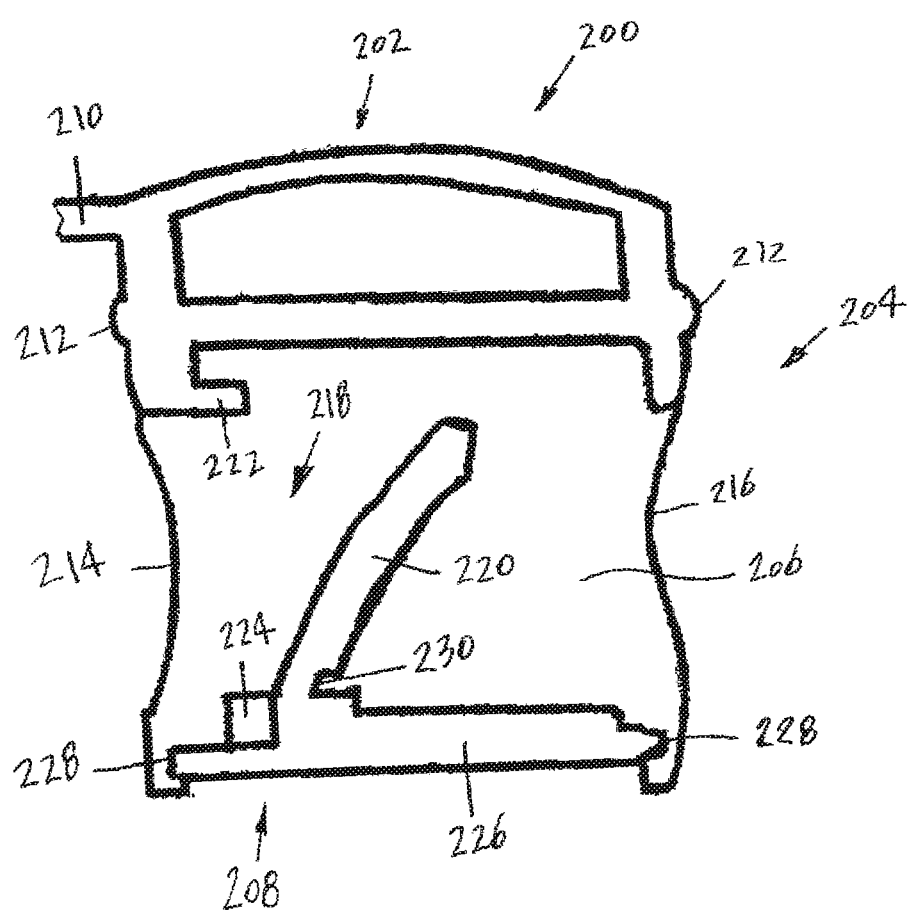
FIG. 11 is a partial cross-sectional view of the valve sealing device shown in FIG. 10 having a check valve shown in a partially opened position.

FIGS. 10 and 11 illustrate another embodiment of a rotatable valve sealing body 200 constructed according to the present disclosure. The rotatable valve sealing body 200 is shown in cross-section in both FIGS. 10 and 11. Also, the rotatable valve sealing body 200 may replace the rotatable valve sealing body 22 or 100 and be inserted into the body 12. The rotatable valve sealing body 200 comprises a top 202, a central body portion 204 having a bore 206, and a bottom 208. A portion of a handle 210 is shown which is part of the top 202. The central body portion 204 also has an annular ridge portion 212 near the top 202. As can be appreciated, the annular ridge portion 212 may be used to be inserted into the ring 40 (FIG. 2). The bore 206 is adapted to be aligned with the lumen 28 of the valve body 12. The bore 206 of the rotatable valve sealing body 200 also has a first opening 214 and a second opening 216. The first opening 214 is used to be aligned with the flexible tubing opening 18 (FIG. 1) of the valve body 12. The first opening 214 has a check valve 218 positioned therein to selectively open or close the first opening 214. The check valve 218 is provided for allowing liquid, saliva, or debris to pass from the flexible tubing opening 18, through the flexible tubing 16, the check valve 218, the bore 206, the second opening 216, and out the hose receiving end 20 when the check valve 218 is opened or partially opened, as is shown in FIG. 11. However, the check valve 218 also prevents any liquid, saliva, or debris from passing or traveling from the hose receiving end 20, the second opening 216, the bore 206, and through the check valve 218 when the check valve 218 is closed, as is shown in FIG. 10. The check valve 218 will close when a reduced pressure occurs from an interaction of a mouth of a patient on the flexible tubing 16. As has been indicated, a patient may be requested to close the mouth of the patient around the flexible tubing 16. When this occurs, a reduced pressure results in which a backflow may occur. The check valve 218 is sensitive to this pressure differential and will close to prevent backflow. The second opening 216 is used to be aligned with the opening 30 (FIG. 2) in the valve body 12.

The check valve 218 has a flap portion 220 that seals against a top seat portion 222 and a bottom seat portion 224 that are formed in the body 200. The flap portion 220 is connected to a bottom plate member 226. The bottom plate member 226 snaps into an opening 228 formed in the bottom 208 of the body 200. The flap portion 220 may be connected to the bottom plate member 226 by use of a hinge 230 or by any other suitable connection means. When manufacturing the body 200, the flap portion 220 is inserted into the opening 228 and then the bottom plate member 226 is snapped into place in the opening 228 in the bottom 208. As previously indicated, the check valve 218 is shown in the closed position in FIG. 10 and in the partially opened position in FIG. 11.

Figure 12:
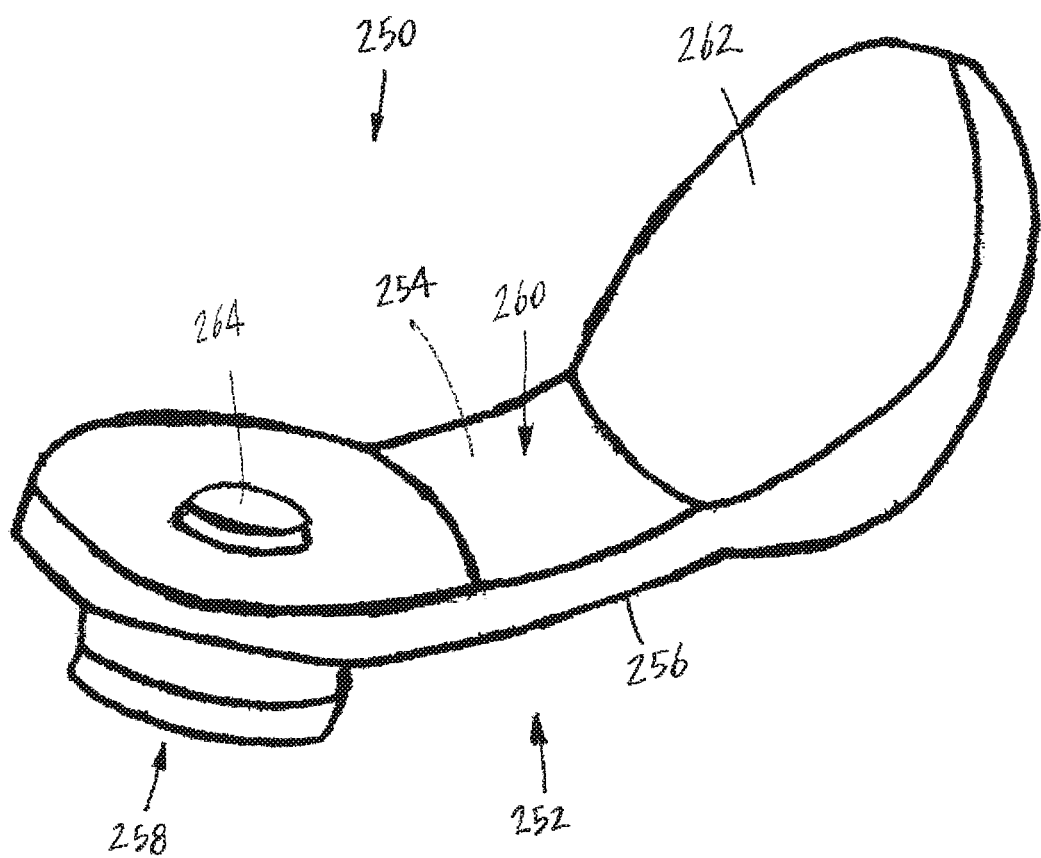
FIG. 12 is a perspective view of cap device constructed according to the present disclosure.

Referring now in particular to FIG. 12, a cap device 250 is depicted which is used to be placed over the opening of a suction tubing, hose, or tailpiece (not shown) when the device 10 is removed from the hose or the tailpiece to dispose the device 10. In this manner, the opening of the hose or the tailpiece will be physically blocked to shut off any air from rushing into the hose to silence any noise produced by the suction system or a source of vacuum. The cap device 250 is sized and shaped to fit over the opening of the hose or the tailpiece. The cap device 250 may be constructed of any suitable material such as rubber or plastic. The valve device 10 may include the cap device 250 so that when the valve device 10 is being removed from the hose for disposal after use the cap device 250 may be placed over the opening of the hose or the tailpiece. The cap device 250 comprises a body portion 252 having a top side 254 and a bottom side 256 with the bottom side 256 having a plug portion 258. A central portion 260 is connected between the body portion 252 and a pull 262. The top side 254 has a raised portion or bump 264. The plug portion 258 is inserted into the opening of the tailpiece or the hose which is connected to a suction source. The pull 262 is used to be grasped by a hand to remove the plug portion 258 and the cap device 250 from the hose or the tailpiece when a new disposable dental valve device 10 is to be used. The plug portion 258 may be of a sufficient size and shape to plug an opening associated with a tailpiece or a hose attached to a source of suction. The cap device 250 may also be provided separately from the device 10. It is also possible that the cap device 250 may be provided as a kit with the device 10.

Figure 13:
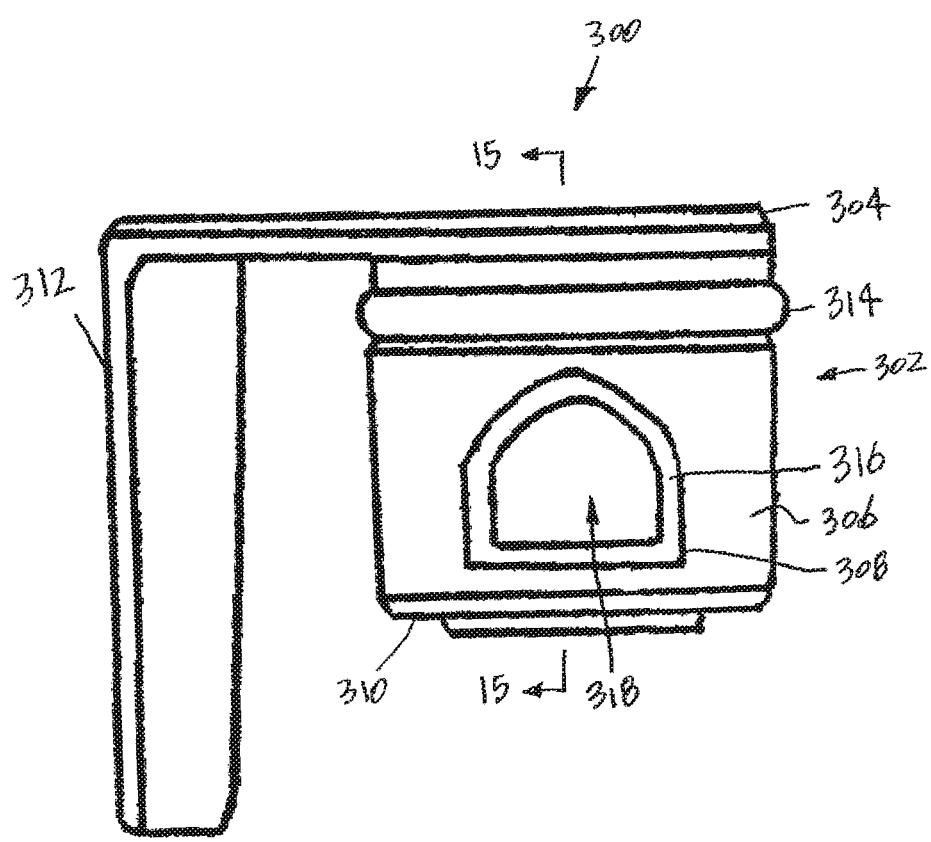
FIG. 13 is a side view of another embodiment of a valve sealing body constructed according to the present disclosure with a check valve in a closed position.

FIG. 13 is a perspective view of another embodiment of a rotatable valve sealing device having a check valve 300. The device 300 is capable of being inserted into the valve body 12 (FIG. 2). The device 300 has a rotatable valve sealing body 302 having a top 304, a central body portion 306 having a bore 308, and a bottom 310. A handle 312 is attached to or part of the top 304. The central body portion 306 also has an annular ridge portion 314 near the top 304. The ridge portion 314 is capable of fitting into the ring 40 (FIG. 2) in a snap fit engagement to secure the device 300 within the valve body 12. The bore 308 is adapted to be aligned with the lumen 28 (FIG. 2) of the valve body 12. The bore 308 of the device 300 also has a first opening 316 that is used to be aligned with the flexible tubing 16 (FIG. 2). In the bore 308 is a check valve 318 positioned therein to selectively open or close the bore 308. The check valve 318 is provided for allowing liquid, saliva, or debris to pass from the flexible tubing opening 18 (FIG. 1), the bore 308, the check valve 318, and out the hose receiving end 20 (FIG. 2) when the check valve 318 is opened. However, the check valve 318 also prevents any liquid, saliva, or debris from passing or traveling from the hose receiving end 20, the bore 308, and through the check valve 318 when the check valve 318 is closed. The check valve 318 will close when a reduced pressure occurs from an interaction of a mouth of a patient on the flexible tubing 16. For example, a patient may be requested to close the mouth of the patient around the flexible tubing 16. When this occurs, a reduced pressure results in which a backflow may occur. The check valve 318 is sensitive to this pressure differential and will close to prevent backflow. The check valve 318 is shown in the closed position in FIG. 13.

Figure 14:
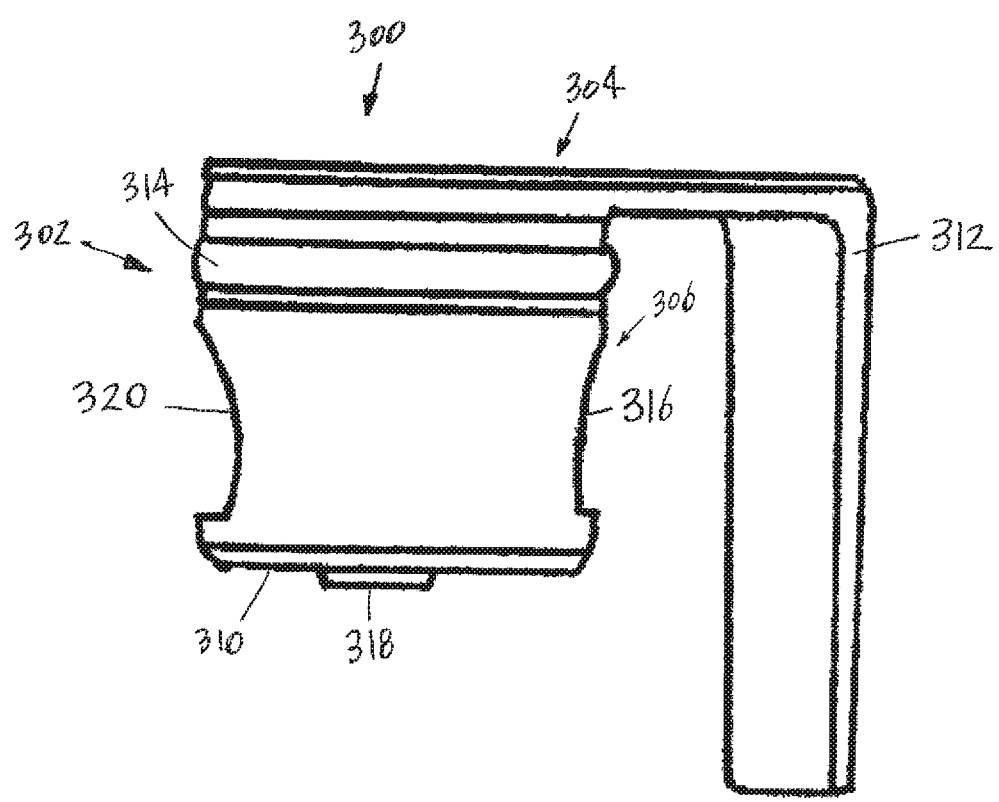
FIG. 14 is another side view of the valve sealing body shown in FIG. 13.

FIG. 14 illustrates a side perspective view of the rotatable valve sealing device 300. The device 300 has a second opening 320 that is used to be aligned with the opening 30 (FIG. 2) of the hose receiving end 20 in the valve body 12. The device 300 is also shown to have the rotatable valve sealing body 302 having the top 304, the central body portion 306, and the bottom 310. The handle 312 is attached to or part of the top 304. The central body portion 306 also has the annular ridge portion 314 near the top 304. The first opening 316 is also shown. The check valve 318 is further shown extending out of the bottom 310 of the device 300, as will be explained in detail further herein.

Figure 15:
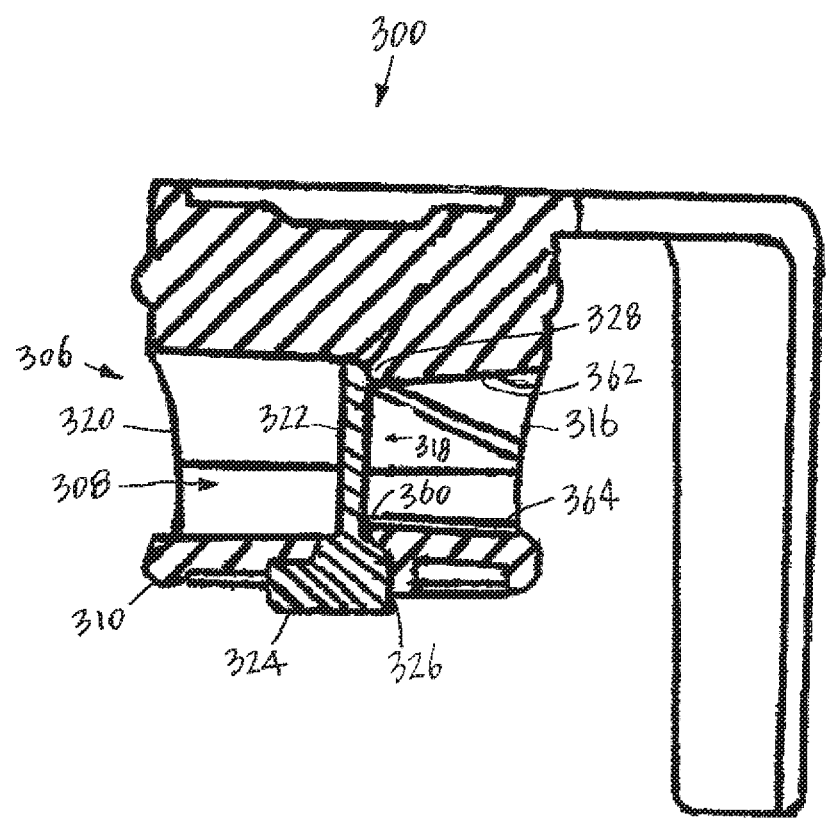
FIG. 15 is a partial cross-sectional view of the valve sealing body shown in FIG. 14.

With particular reference now to FIG. 15, a cross-sectional view of the rotatable valve sealing device shown in FIG. 13 taken along the plane of line 15-15 is shown. The device 300 has the bore 308 that extends through the central body portion 306 between the first opening 316 and the second opening 320. The check valve 318 comprises a flap portion 322 and a retention portion 324. The check valve 318 is inserted into the bore 308 through an opening 326 formed in the bottom 310. As can be appreciated, the check valve 318 is located within the bore 308 and offset from the first opening 316. The retention portion 324 is retained against the bottom 310. The bore 308 has an upper seat or stop portion 328 against which the flap portion 322 may be positioned when in the closed position, as is shown in FIG. 15. The upper stop portion 328 prevents the flap portion 322 from moving past a vertical position or toward the first opening 316. In this manner, when a reduced pressure occurs from an interaction of a mouth of a patient on the flexible tubing 16 (FIG. 1) the flap portion 322 of the check valve 318 will press against the upper stop portion 328 and prevent a backflow condition from occurring. The flap portion 322 prevents any liquid, blood, saliva, or debris present in the suction system, the hose, or the bore 308 from flowing into a mouth of a patient. The bore 308 may also be comprised having a lower seat or stop portion 360 against which the flap portion 322 may be positioned when in the closed orientation. The bore 308 has an upper slanted surface 362 that slants downward from the first opening 316 toward the upper stop portion 328. The bore 308 also has a lower slanted surface 364 that slants upwardly from the first opening 316 toward the lower stop portion 360. Also, the first opening 316 may be smaller in diameter than the second opening 320.

Figure 16:
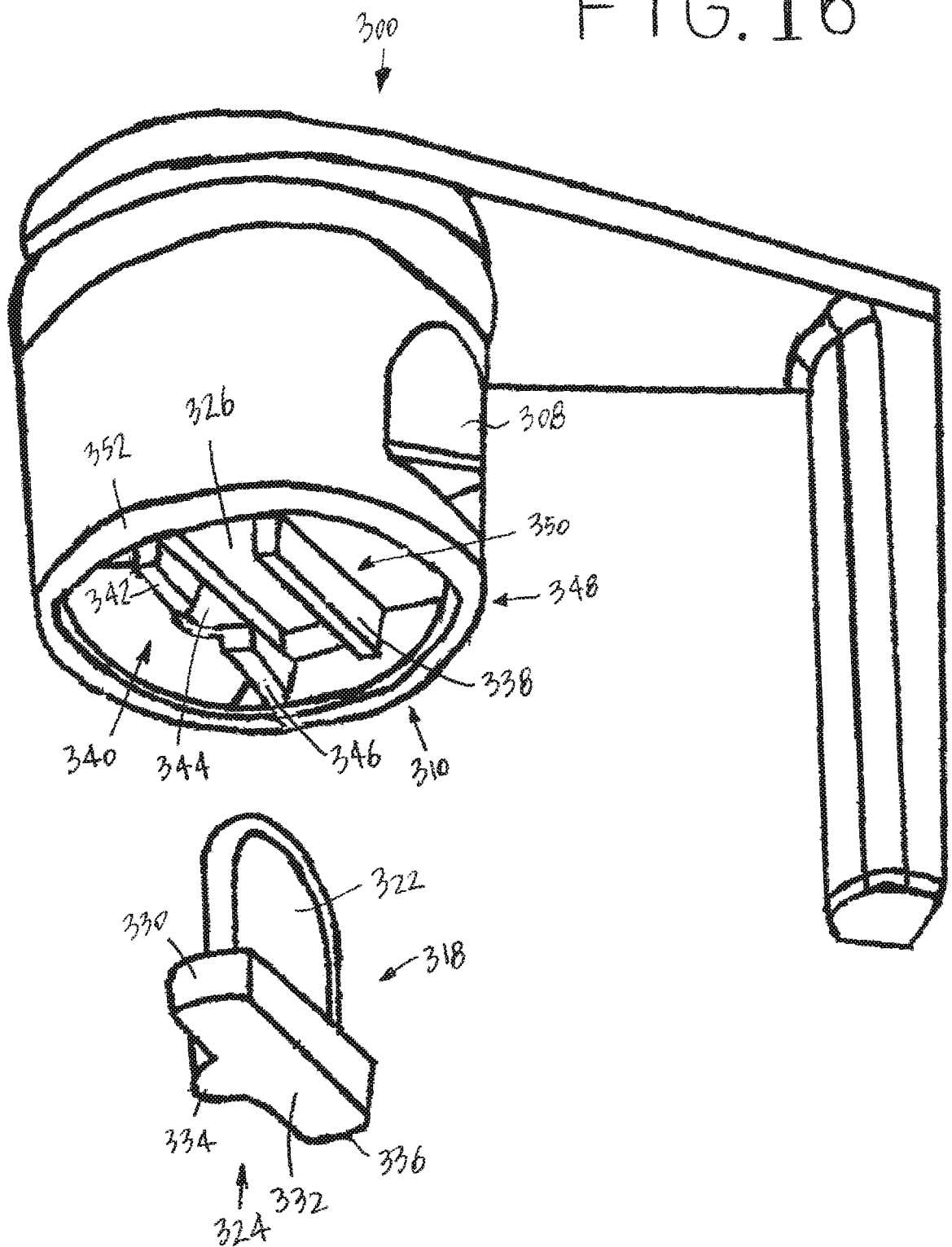
FIG. 16 is an exploded view of the valve sealing body shown in FIG. 13.

With reference now to FIG. 16, an exploded view of the rotatable valve sealing device 300 is shown. In this particular view, the check valve 318 has been removed from the bore 308 and the opening 326 formed in the bottom 310. The check valve 318 has the flap portion 322 and the retention portion 324. The flap portion 322 is generally hemispherical or semicircular in shape. The retention portion 324 has a first end 330, a central portion 332 having an extension member 334, and a second end 336. The bottom 310 of the device 300 has the opening 326, a first ledge member 338, and a second ledge member 340 having a first ledge portion 342, a central indented ledge portion 344, and a second ledge portion 346. The central indented ledge portion 344 is for capturing the extension member 334 to retain the retention portion 324 in the bottom 310 of the device 300. The first ledge member 338 and the second ledge member 340 are also used to hold the retention portion 324 in place on the bottom 310 of the device 300. The flap portion 322 is sized and shaped to fit through the opening 326 to slide the flap portion 322 in place within the bore 308. The bottom 310 has an annular ring 348 formed in the bottom 310. A central indentation 350 is formed within the annular ring 348. The annular ring 348 has a surface 352 that contacts an interior surface (not shown) of the bottom 36 of the valve body 12. The annular ring 348, the central indentation 350, and the surface 352 facilitate smooth and easy rotation of the rotatable valve sealing body 300 within the valve body 12. The annular ring 348, the central indentation 350, and the surface 352 further allow rotation of the body 300 without being bound up within the valve body 12. The surface 352 may also be eased or chamfered.

In operation of the device 10, with any of the rotatable valve sealing devices 100, 200, or 300 installed within the valve body 12, the hose receiving end 20 of the device 10 is placed on to a hose connected to a suction system and the flexible tubing 16 may be placed in a mouth of a dental patient. Any of the handles 110, 210, or 312, which may include an indicator to indicate the closed position and the open position, may be manually operated to open the device 10. Once in the open position, air is allowed to flow through the flexible tubing opening 18, the flexible tubing 16, the lumen 28, the rotatable valve sealing body 100, 200, or 300, the hose receiving end 20 and into a suction system. In the event that reduced pressure occurs from an interaction of a mouth of a patient on the flexible tubing 16, the check valve 118, 218, or 318 will close and no backflow will be allowed from the suction system or the valve device 10. When suction is not needed during a dental procedure, the device 10 is closed. Further, once a dental procedure has been completed and the device 10 is in the closed position, the device 10 is easily separated from the hose. Once the device 10 is disconnected from the hose, the device 10 may be disposed of by any suitable manner. A new device 10 is then connected to the hose and another dental procedure may be initiated. As can be appreciated, the device 10 does not require that a separate low volume ejector or a high volume evacuator be used.

The disposable dental valve device 10 and the various other components, such as the rotatable valve bodies 22, 100, 200, and 300, may be formed of any suitable material such as plastic, polyethylene, and high density polyethylene or any other suitable material that is disposable and recyclable. It is also possible that the device 10 and the bodies 22, 100, 200, and 300 may be constructed of a material that will allow the device 10 and the bodies 22, 100, 200, and 300 to be discarded after a single use. Any suitable plastic may be used to construct the device 10 and the bodies 22, 100, 200, and 300 so that the device 10 may withstand use in a dental operation or procedure. It is also possible and contemplated to incorporate an antimicrobial agent or chemical in the plastic or to provide a coating of an antimicrobial agent on the plastic to further prevent cross-contamination when using the device 10. As can be appreciated, the antimicrobial agent may be incorporated into any of the components of the device 10.

From all that has been said, it will be clear that there has thus been shown and described herein a dental valve device which fulfills the various advantages sought therefore. It will become apparent to those skilled in the art, however, that many changes, modifications, variations, and other uses and applications of the subject dental valve device are possible and contemplated. All changes, modifications, variations, and other uses and applications which do not depart from the spirit and scope of the disclosure are deemed to be covered by the disclosure, which is limited only by the claims which follow.

What is claimed is:

1. A dental valve device comprising:
   a valve body having a tip receiving end, a flexible tubing extending outwardly from the tip receiving end with the flexible tubing having a flexible tubing opening, a hose receiving end, a lumen formed between the flexible tubing opening and the hose receiving end, a partial opening formed in the valve body; and
   a rotatable valve sealing body adapted to be inserted into the partial opening, the rotatable valve sealing body having a bottom having an opening, a bore for alignment with the lumen formed between the flexible tubing opening and the hose receiving end, the bore having a tip receiving opening and a hose receiving opening and a check valve positioned in the bore and the opening in the bottom of the rotatable valve sealing body.

2. The dental valve device of claim 1 wherein the rotatable valve sealing body further comprises a lower end having an annular ring having a surface and an indentation formed within the annular ring.

3. The dental valve device of claim 1 wherein the rotatable valve sealing body further comprises a top and an annular ridge portion is positioned near the top.

4. The dental valve device of claim 1 wherein the rotatable valve sealing body and the valve body are each constructed of plastic.

5. The dental valve device of claim 1 wherein the rotatable valve sealing body further comprises a top and a handle portion connected to the top.

6. The dental valve device of claim 1 wherein the tip receiving opening and the hose receiving opening of the rotatable valve sealing body are concave.

7. The dental valve device of claim 1 further comprising an exterior rib.

8. A dental valve device comprising:
   a valve body having a tip receiving end, a flexible tubing extending outwardly from the tip receiving end with the flexible tubing having a flexible tubing opening, an exterior rib, a hose receiving end, a lumen formed between the tip receiving end and the hose receiving end, a partial opening formed in the valve body; and
   a rotatable valve sealing body adapted to being inserted into the partial opening, the rotatable valve sealing body having a bottom having an opening, a bore for alignment with the lumen formed between the tip receiving end and the hose receiving end, the bore having a tip receiving opening and a hose receiving opening, and the rotatable valve sealing body having a check valve positioned in the bore and the opening in the bottom of the rotatable valve sealing body, the check valve further comprising a flap portion and a retention portion.

9. The dental valve device of claim 8 wherein the rotatable valve sealing body further comprises an upper seat against which the flap portion may be positioned.

10. The dental valve device of claim 9 wherein the flap portion is movable between an opened position and a closed position.

11. The dental valve device of claim 9 wherein the rotatable valve sealing body further comprises a lower seat against which the flap portion may be positioned.

12. The dental valve device of claim 8 wherein the rotatable valve sealing body and the valve body are each constructed of plastic.

13. The dental valve device of claim 8 wherein an antimicrobial agent is incorporated into the dental valve device.

14. The dental valve device of claim 8 wherein the bottom of the rotatable valve sealing body further comprises a first ledge member, a second ledge member having a first ledge portion, a central indented ledge portion, and a second ledge portion, and wherein the flap portion is positioned in the bore and the retention portion is retained against the bottom of the rotatable valve sealing body, the retention portion having a first end, a central portion having an extension member, and a second end with the first end and the second end for being positioned between the first ledge member and the second ledge member and the extension member for fitting into the central indented ledge portion.

15. A dental valve device kit comprising:
   a valve body having a tip receiving end, a flexible tubing extending outwardly from the tip receiving end with the flexible tubing having a flexible tubing opening, a hose receiving end, a lumen formed between the flexible tubing opening and the hose receiving end, a partial opening formed in the valve body;
   a rotatable valve sealing body adapted to be inserted into the partial opening, the rotatable valve sealing body having a bottom having an opening, a bore for alignment with the lumen formed between the flexible tubing opening and the hose receiving end, the bore having a tip receiving opening and a hose receiving opening and a check valve positioned in the bore and the opening in the bottom of the rotatable valve sealing body; and
   a cap device for insertion into a hose connected to a source of vacuum.

16. The dental valve device kit of claim 15 wherein the cap device comprises a body portion having a top side and a bottom side with the bottom side having a plug portion, a pull, and a central portion connected between the body portion and the pull.

17. The dental valve device kit of claim 15 wherein the cap device is constructed of rubber.

18. The dental valve device kit of claim 15 wherein the cap device is constructed of plastic.

19. The dental valve device kit of claim 15 wherein an antimicrobial agent is incorporated into the cap device.

20. The dental valve device of claim 15 wherein the rotatable valve sealing body and the valve body are each constructed of plastic.

* * * * *